US010631937B2

(12) United States Patent
Tyulmankov et al.

(10) Patent No.: US 10,631,937 B2
(45) Date of Patent: Apr. 28, 2020

(54) SYSTEMS AND METHODS FOR DETERMINING ORIENTATION OF AN IMPLANTED ELECTRICAL STIMULATION LEAD

(71) Applicant: Boston Scientific Neuromodulation Corporation, Valencia, CA (US)

(72) Inventors: Danil Tyulmankov, Stamford, CT (US); Hemant Bokil, Santa Monica, CA (US)

(73) Assignee: BOSTON SCIENTIFIC NEUROMODULATION CORPORATION, Valencia, CA (US)

(*) Notice: Subject to any disclaimer, the term of this patent is extended or adjusted under 35 U.S.C. 154(b) by 89 days.

(21) Appl. No.: 15/945,086

(22) Filed: Apr. 4, 2018

(65) Prior Publication Data
US 2018/0296279 A1 Oct. 18, 2018

Related U.S. Application Data

(60) Provisional application No. 62/485,620, filed on Apr. 14, 2017.

(51) Int. Cl.
| | |
|---|---|
| *G06K 9/00* | (2006.01) |
| *A61B 34/20* | (2016.01) |
| *A61B 17/34* | (2006.01) |
| *A61B 90/00* | (2016.01) |
| *A61N 1/05* | (2006.01) |
| *A61N 1/372* | (2006.01) |

(52) U.S. Cl.
CPC .......... *A61B 34/20* (2016.02); *A61B 17/3468* (2013.01); *A61B 90/39* (2016.02); *A61B 2034/2065* (2016.02); *A61B 2090/376* (2016.02); *A61B 2090/3966* (2016.02); *A61B 2090/3983* (2016.02); *A61N 1/05* (2013.01); *A61N 1/0551* (2013.01); *A61N 1/372* (2013.01)

(58) Field of Classification Search
CPC ....................................................... A61B 34/20
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| (Continued) | | |

OTHER PUBLICATIONS

D'Albis et al (NPL"PyDBS: an automated image processing workflow for deep brain stimulation surgery", Received: Jan. 10, 2014 / Accepted: Apr. 9, 2014 / Published online: May 6, 2014) (Year: 2014).*

*Primary Examiner* — Oneal R Mistry
(74) *Attorney, Agent, or Firm* — Lowe Graham Jones PLLC; Bruce E. Black

(57) ABSTRACT

A method for identifying a rotational orientation of a lead includes obtaining a radiological image of the lead having a lead body, a distal tip, electrodes, and an asymmetric marker, where the lead defines a lead axis along the portion of the lead extending from the distal tip and including the electrodes and the asymmetric marker; determining, using the set of lead slices and the set of marker slices, a direction vector extending from an estimated lead axis and passing through a determined center of weighted mass of the lead; and providing an indication of a direction of the direction vector on a display.

20 Claims, 12 Drawing Sheets

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 8/2004 | Meadows et al. |
| 6,895,280 B2 | 5/2005 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,650,184 B2 | 1/2010 | Walter |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,473,061 B2 | 6/2013 | Moffitt et al. |
| 8,571,665 B2 | 10/2013 | Moffitt et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,037,256 B2 | 5/2015 | Bokil et al. |
| 2007/0150036 A1 | 6/2007 | Anderson |
| 2007/0197896 A1* | 8/2007 | Moll ............... A61B 1/00039 600/407 |
| 2009/0187222 A1 | 7/2009 | Barker |
| 2009/0204192 A1 | 8/2009 | Carlton et al. |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2010/0030298 A1 | 2/2010 | Martens et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0257707 A1 | 10/2011 | Kothandaraman |
| 2011/0313500 A1 | 12/2011 | Barker et al. |
| 2012/0016378 A1 | 1/2012 | Pianca et al. |
| 2012/0046531 A1* | 2/2012 | Hua ............... A61B 5/6865 600/317 |
| 2012/0046710 A1 | 2/2012 | DiGiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0314919 A1 | 12/2012 | Sparks et al. |
| 2012/0314924 A1 | 12/2012 | Carlton et al. |
| 2012/0316615 A1 | 12/2012 | DiGiore et al. |
| 2013/0039550 A1 | 2/2013 | Blum et al. |
| 2013/0105071 A1 | 5/2013 | DiGiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0267837 A1 | 10/2013 | Schulte et al. |
| 2014/0039587 A1 | 2/2014 | Romero |
| 2014/0122379 A1 | 5/2014 | Moffitt et al. |
| 2014/0228921 A1 | 8/2014 | Howard |
| 2014/0257428 A1 | 9/2014 | Zhu |
| 2014/0276002 A1 | 9/2014 | West et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2014/0371819 A1 | 12/2014 | Goetz et al. |
| 2015/0018915 A1 | 1/2015 | Leven |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0157851 A1 | 6/2015 | Sefkow et al. |
| 2016/0030749 A1 | 2/2016 | Carcieri et al. |
| 2016/0228692 A1 | 8/2016 | Steinke et al. |
| 2017/0056678 A1 | 3/2017 | Bokil |
| 2017/0061627 A1 | 3/2017 | Bokil |
| 2017/0348061 A1* | 12/2017 | Joshi ............... A61B 17/7089 |
| 2018/0104472 A1 | 4/2018 | Govea et al. |
| 2018/0104482 A1 | 4/2018 | Bokil |
| 2018/0169415 A1* | 6/2018 | Seeley ............... A61N 1/0534 |

\* cited by examiner

SYSTEMS AND METHODS FOR DETERMINING ORIENTATION OF AN IMPLANTED ELECTRICAL STIMULATION LEAD

CROSS-REFERENCE TO RELATED APPLICATIONS

This application claims the benefit under 35 U.S.C. § 119(e) of U.S. Provisional Patent Application Ser. No. 62/485,620, filed Apr. 14, 2017, which is incorporated herein by reference.

FIELD

The present invention is directed to the area of implantable electrical stimulation systems and methods of making and using the systems. The present invention is also directed to systems and methods for determining the orientation of an implanted electrical stimulation lead.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a method for identifying a rotational orientation of an implanted electrical stimulation lead. The method includes generating, from a radiological image of a distal portion of a lead, a set of lead slices and a set of marker slices, the lead including a lead body, a distal tip, electrodes disposed along a distal portion of the lead body, and an asymmetric marker disposed along the distal portion of the lead body, the electrodes comprising segmented electrodes that each extend around no more than 50% of a circumference of the lead body, where the lead defines a lead axis extending along a portion of the lead that extends from the distal tip and includes the plurality of electrodes and the asymmetric marker; determining, using the set of lead slices and the set of marker slices, a direction vector extending from an estimated lead axis and passing through a determined center of weighted mass of the lead; and providing an indication of a direction of the direction vector on a display In at least some embodiments, the set of lead slices are generated to each extend through the distal portion of the lead transverse to the lead axis at a longitudinal position along the lead ranging from the distal tip to a proximal edge of a proximal-most one of the electrodes. In at least some embodiments, the set of marker slices are generated to each extend through the distal portion of the lead transverse to the lead axis at a longitudinal position along the lead where the marker window is disposed.

In at least some embodiments, determining, using the set of lead slices and the set of marker slices, a direction vector extending from an estimated lead axis and passing through a determined center of weighted mass of the lead includes determining, using the set of lead slices and the set of marker slices, an average-intensity-difference slice; determining the estimated lead axis of the lead within the average-intensity-difference slice; and determining the center of weighted mass of the lead within the average-intensity-difference slice. In at least some embodiments, each of the lead slices and marker slices is arranged as an array of pixels with pixel locations within the array being identical for all of the lead slices and marker slices.

In at least some embodiments, determining an estimated lead axis of the lead within the average-intensity-difference slice includes obtaining a lead-tip estimate. In at least some embodiments, obtaining a lead-tip estimate includes performing lead-tip-correction to generate a corrected lead-tip estimate. The lead-tip-correction includes (a) estimating, for an intermediately-positioned lead slice of the set of lead slices, an outer edge of the lead; (b) determining, for the intermediately-positioned lead slice, a total intensity value of all the pixels located within the estimated outer edge of the lead; (c) selecting a first lead slice, of the set of lead slices, distal to the intermediately-positioned lead slice as a current lead-tip estimate; (d) estimating, for the first lead slice, an outer edge of the lead; (e) determining, for the first lead slice, a total intensity value of all the pixels located within the estimated outer edge of the lead; and (f) setting the first lead slice as the corrected lead-tip estimate when the total intensity value for the first lead slice is less than a threshold percentage of the total intensity value for the intermediately-positioned lead slice, or updating a location of the current lead-tip estimate to a different lead slice, of the set of lead slices, that is positioned more distally along the lead from the first lead slice when the total intensity value for the first lead slice is equal to or greater than the threshold percentage of the total intensity value for the intermediately-positioned lead slice. In at least some embodiments, (a) estimating, for an intermediately-positioned lead slice, an outer edge of the lead includes selecting an intermediately-positioned lead slice located at a midpoint along the lead between the distal tip and a proximal edge of the proximal-most electrode. In at least some embodiments, estimating an outer edge of the lead for each of steps (a) and (c) includes performing an edge-detection technique. In at least some embodiments, (e) setting the first lead slice as the corrected lead-tip estimate includes setting a determined centroid of the first lead slice as the corrected lead-tip estimate.

In at least some embodiments, determining an estimated lead axis of the lead within the average-intensity-difference slice includes performing lead-axis correction to generate a corrected lead-axis estimate. The lead-axis-correction includes (a) obtaining a current lead-axis estimate; (b) estimating, for each lead slice of the set of lead slices, an outer edge of the lead for that slice; (c) determining, for each lead slice of the set of lead slices, a centroid for the pixels within the estimated outer edge of the lead; (d) determining a best-fit three-dimensional axis for the determined centroids to provide an updated lead-axis estimate; and (e) setting the updated lead-axis estimate as the corrected lead axis when an angle between the current lead-axis estimate and the updated lead-axis estimate meets a threshold criterion, or when the threshold criterion is not met, replacing the current lead-axis estimate with the updated lead-axis estimate. In at least some embodiments, determining a best-fit three-dimensional axis for the calculated centroids to provide an updated lead-axis estimate includes performing a three-dimensional orthogonal distance regression. In at least some embodiments, setting the updated lead-axis estimate as the corrected lead axis when an angle between the current lead-axis estimate and the updated lead-axis estimate meets a threshold criterion includes setting the updated lead-axis estimate as the corrected lead axis when an angle between the current lead-axis estimate and the updated lead-axis estimate is less than 0.5 degrees. In at least some embodiments, replacing the current lead-axis estimate with the updated lead-axis estimate includes repeating steps (b) through (e).

In at least some embodiments, determining, using the set of lead slices and the set of marker slices, an average-intensity-difference slice includes determining, for the set of lead slices, an average-lead-intensity at each pixel location to obtain an average-lead-intensity slice; determining, for the set of marker slices, an average-marker-intensity at each pixel location to obtain an average-marker-intensity slice; and subtracting, for each pixel location, the average-lead-intensity from the average-marker-intensity to determine an average-intensity-difference slice. In at least some embodiments, determining, using the set of lead slices and the set of marker slices, an average-intensity-difference slice further includes setting to zero every pixel of each of the average-lead-intensity slice and the average-marker-intensity slice having a negative intensity value.

In at least some embodiments, determining a center of weighted mass of the lead within the average-intensity-difference slice includes determining, for the average-intensity-difference slice, an estimated outer edge of the lead; determining an inner edge of the asymmetric marker to define a region of interest within which the asymmetric marker is located; and calculating the center of weighted mass of the region of interest. In at least some embodiments, determining a center of weighted mass of the lead within the average-intensity-difference slice further includes thresholding the region of interest at a predetermined level to remove dark areas within the region of interest prior to calculating the center of weighted mass of the region of interest. In at least some embodiments, determining, for the average-intensity-difference slice, an estimated outer edge of the lead includes performing an edge-detection technique.

Another embodiment is a system for identifying a rotational orientation of an implanted electrical stimulation lead. The system includes a computer processor configured and arranged to perform any of the methods described above.

Yet another embodiment is a non-transitory computer-readable medium having processor-executable instructions stored thereon that, when executed by a processor, cause the processor to perform any of the methods described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to systems and methods for determining the orientation of an implanted electrical stimulation lead.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, or stimulation of other nerves, muscles, and tissues.

Figure 1:
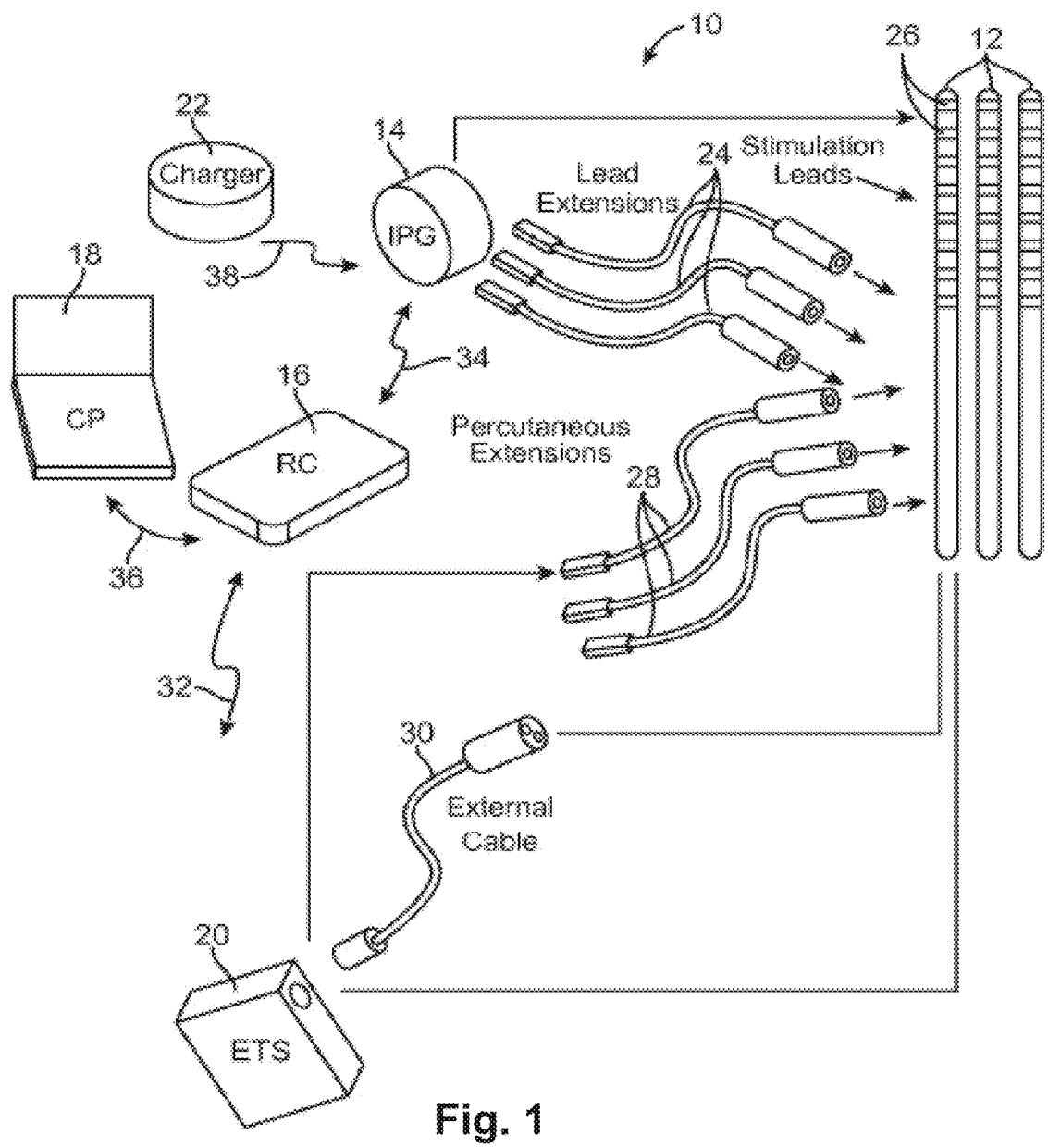
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
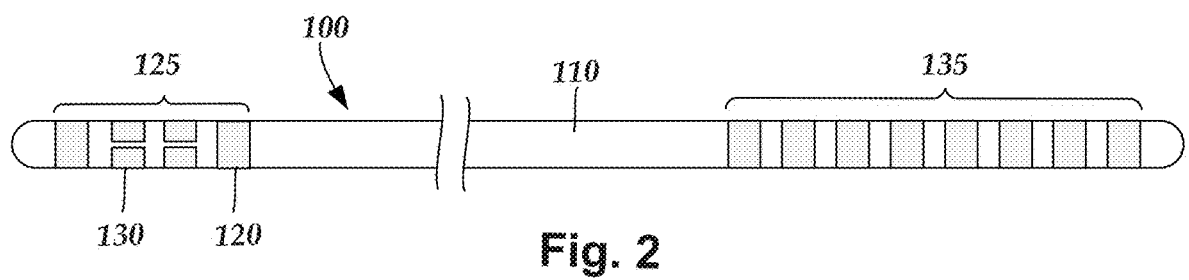
FIG. 2 is a schematic side view of one embodiment of an electrical stimulation lead, according to the invention.

FIG. 2 illustrates one embodiment of a lead 110 with electrodes 125 disposed at least partially about a circumference of the lead 110 along a distal end portion of the lead and terminals 135 disposed along a proximal end portion of the lead. The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 125 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent applications Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

In many instances, it is important to identify the orientation (i.e., pitch, yaw, and roll) of a lead with segmented electrodes when the lead is implanted into the patient (for example, in the brain of a patient.) Knowing the rotational, or "longitudinal", orientation (i.e., roll) of the lead (and, in particular, the rotational directions of one or more of the individual segmented electrodes) can facilitate determining where segmented electrodes may be situated for stimulating a particular anatomical or physiological tissue target or determining an expected direction of the electrical stimulation field that can be generated by each of the segmented electrodes. It may be difficult to determine rotational orientation radiologically because the segmented electrodes are typically positioned along the lead in a rotationally symmetric configuration.

To facilitate radiological identification of a rotational orientation, the lead can include a rotationally asymmetric marker. The asymmetric marker may, optionally, be made of different material (for example, a conductive material such as metal) from the lead body so that the marker and lead body are radiologically distinguishable. The asymmetric nature of the marker may make it distinguishable even when made of the same material as the lead body. For example, the asymmetric marker may include a bump or depression that is radiologically identifiable.

Figure 3:
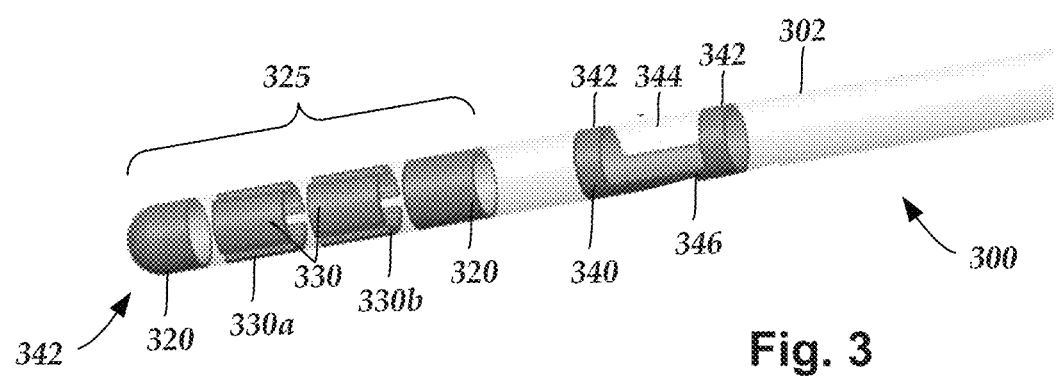
FIG. 3 is a schematic diagram of one embodiment of the distal portion of a lead with an asymmetric marker, according to the invention.

FIG. 3 illustrates one embodiment of a distal portion of a lead 300 with a lead body 302, a distal tip 342, and electrodes 325 including one or more optional ring electrodes 320 and multiple segmented electrodes 330. The lead 300 also includes a marker 340 that is asymmetrically shaped. The asymmetric marker 340 is made of a material that is substantially different from the material of the lead body 302, particularly, when viewed using a radiological imaging technique, such as CT imaging, so that the asymmetric marker is radiologically distinguishable from the lead body. In at least some embodiments, the asymmetric marker 340 is made of metal (such as a pure metal or an alloy) and, in at least some embodiments, is made of the same material as the electrodes 325. In other embodiments, the asymmetric marker 340 is made of the same material as the lead body.

In at least some embodiments, the asymmetric marker 340 defines one or more optional rings 342 formed around the entire circumference of the lead 300, at least one window 344, and a longitudinal band 346 disposed opposite the window. In at least some embodiments, the longitudinal band 346 of the marker 340 extends around no more than 80%, 75%, 67%, 60%, 50%, 40%, 34%, 30%, 25%, or 20% of the circumference of the lead with the window 344 extending around the remainder of the circumference. In at least some embodiments, the longitudinal band 346 of the asymmetric marker 340 is aligned with at least one of the segmented electrodes 330 (such as segmented electrodes 330*a*, 330*b* in the illustrated embodiment of FIG. 3.) In the illustrated embodiments, the longitudinal band 346 extends between two rings 342. Examples of other markers that can be used in place of asymmetric marker 340 can be found in U.S. Provisional Patent Application Ser. No. 62/408,392. The asymmetric marker 340 is shown positioned proximally from the electrodes 325. In alternate embodiments, the asymmetric marker 340 is positioned distally from the electrodes, or at a position that is proximal to the distal-most electrode and distal to the proximal-most electrode.

Figure 4:
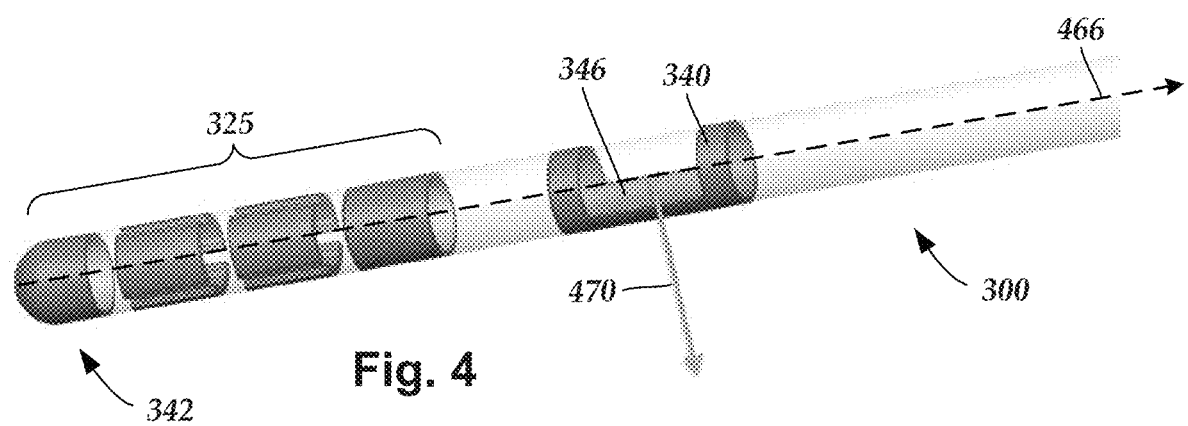
FIG. 4 is a schematic diagram of one embodiment of the distal portion of a lead with an asymmetric marker and a direction vector extending outwardly from lead in a direction corresponding to the directionality of the asymmetric marker, according to the invention.

Turning to FIG. 4, a method is described below for determining the rotational orientation (i.e., roll) of the lead using radiological imaging, such as CT. The method uses information obtained from a three-dimensional radiological image of a portion of an implanted lead that includes both the electrodes and asymmetric marker to generate a direction vector extending from a determined lead axis to a calculated "center" (e.g., center of weighted mass, center-of-mass, calculated center-of-mass, or the like). The direction vector indicates the rotational orientation of the lead by indicating the directionality of the asymmetric marker. As mentioned above, the directionality of the asymmetric marker is known with respect to the segmented electrode(s).

The generated direction vector can be used to determine the volume of activation of the lead relative to the patient's anatomy. Determining the volume of activation may be advantageous to enable targeting of specific regions (e.g., within the patient's brain) directly, without the need to create clinical effects maps or performing monopolar review, which can be time-consuming and tedious.

FIG. 4 illustrates one embodiment of a distal portion of the lead 300. A lead axis is indicated by dashed and arrowed line 466, and a direction vector 470 is shown extending perpendicularly from the lead axis 466 and through a calculated "center" of the lead. As shown in FIG. 4, the direction vector corresponds to the directionality of the asymmetric marker 340. It will be understood that the lead axis of interest is along the electrode-containing portion of the lead. The lead axis may not be consistent along an entire longitudinal length of the lead, as intermediate portions of the lead may curve and extend in different directions. Consequently, the lead axis shown in FIG. 4, and as used in the below-described process, extends along the distal portion of the lead from the distal tip 342 of the lead and includes the asymmetric marker 340 and the electrodes 325.

Figure 5A:
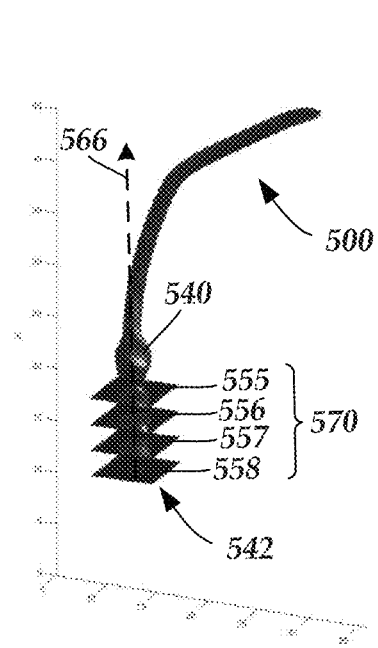
FIG. 5A is a schematic diagram of one embodiment of an isosurface image of a distal portion of a lead with a set of lead slices extending through electrode-containing portions of the lead, according to the invention.
Figure 5C:
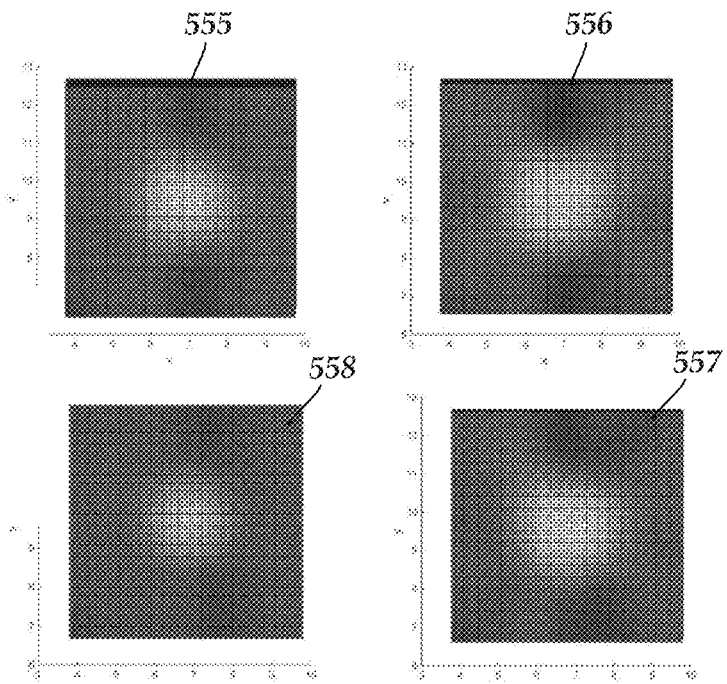
FIG. 5C is a schematic top view of one embodiment of the set of lead slices of FIG. 5A, according to the invention.
Figure 5B:
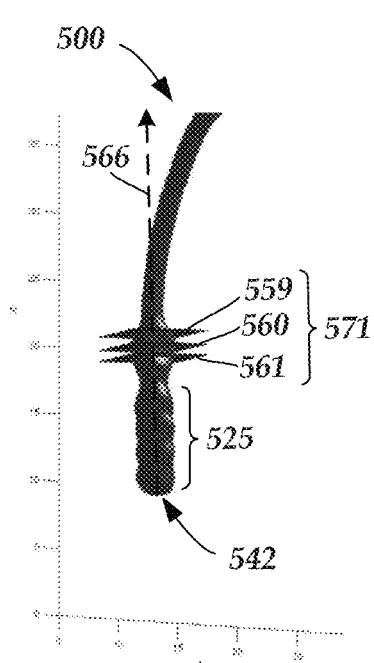
FIG. 5B is a schematic diagram of one embodiment of an isosurface image of a distal portion of a lead with a set of marker slices extending through marker-containing portions of the lead, according to the invention.

Turning to FIGS. 5A and 5B, radiological imaging, such as computed tomography ("CT") imaging, can be used to generate isosurface images. An isosurface image from CT image (or other radiological image) data can be generated, for example, by combining image data from a set of slices to form a volume and then selecting those portions of the resulting volume that have the same intensity (or fall within the same narrow band of intensities), or other image parameter. In the example of CT imaging, the intensity (measured in Hounsfield Units) is often related to the absorption of x-rays by the material being imaged. For example, the asymmetric marker 340 made of metal will typically have a higher absorption of x-rays than the lead body 302, which is formed of a polymeric material. An isosurface image, generated from the corresponding CT images by selecting a single intensity or narrow band of intensities, can be used to identify those portions of the lead that are formed of metal, such as the asymmetric marker 340 or the electrodes 325, or both.

FIGS. 5A and 5B illustrate isosurface images from CT scans of a distal portion of a lead 500 having a distal tip 542 and including electrodes 525 (some of which being segmented) and an asymmetric marker 540. The illustrated embodiment shows imaging slices 555-561 extending through the lead approximately transversely (i.e., perpendicular) to a lead axis 566. The imaging slices 555-561 are generated from the volume obtained by an imager (e.g., a CT scanner). The determination of the perpendicular imaging-slice plane is based on the current best estimate of the lead axis. This estimate may be updated during execution of the below-described method. It is unlikely that the slices will extend along any of the basis vectors of the CT coordinate system. Consequently, it may be necessary to perform interpolation to approximately determine the transverse plane. Once the lead axis 566 is determined, the transverse plane is normal (i.e. perpendicular) to the lead axis. The locations of the pixels in the transverse plane may not correspond to the locations of the pixels in the original CT coordinate system. In which case, interpolation may be used to determine the values of the pixels along the plane transverse to the lead.

The imaging slices includes a set of lead slices 570 that extend through the distal portion of the lead and include the portion of the lead along which the electrodes 525 are disposed. FIG. 5A shows the set of lead slices 570 including four lead slices 555-558. The lead slices 555-558 are shown extending (transverse to the lead axis) through a portion of the lead extending from the distal tip 542 to a distal end of the proximal-most electrode.

The imaging slices also includes a set of marker slices 571 that extend (transverse to the lead axis) through the portion of the lead along which the asymmetric marker 540 is disposed. FIG. 5B shows the set of marker slices 571 including three marker slices 559-561. The marker slices 559-561 are shown extending through a portion of the lead along which the window (344 in FIG. 3) of the asymmetric marker 540 is disposed.

The number of imaging slices may vary. It is typically useful for the number of imaging slices to be high enough to avoid throwing out useful information, yet small enough to avoid being unnecessarily redundant. The number of imaging slices may also depend on the resolution of the CT scanner, as well as the angle of the lead axis relative to the CT axes. The number of imaging slices shown extending through the lead in FIGS. 5A-5B is exemplary and for illustrative purposes only. In at least some embodiments, the set of lead slices 570 has 100 slices. In at least some embodiments, the set of marker slices 571 has 10 slices.

Figure 5D:
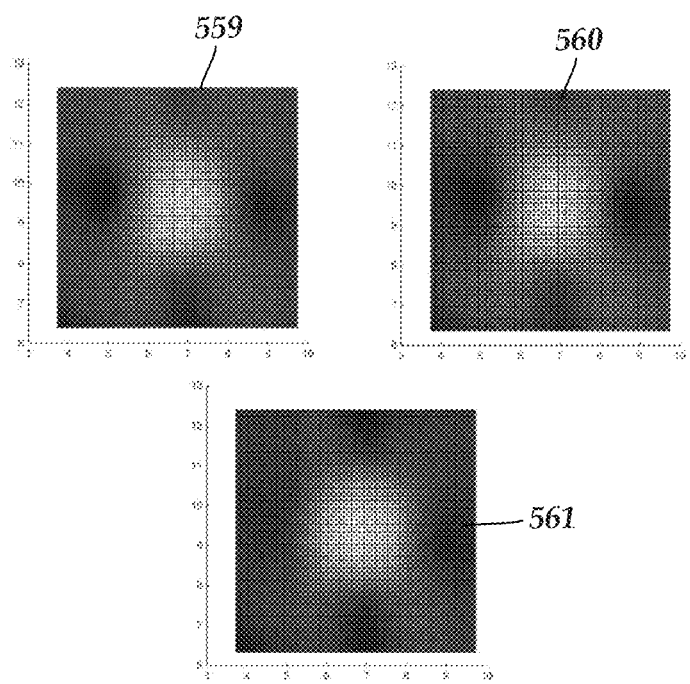
FIG. 5D is a schematic top view of one embodiment of the set of marker slices of FIG. 5B, according to the invention.

FIG. 5C illustrates a top view of the four lead slices 555-558 of FIG. 5A. FIG. 5D illustrates a top view of the three marker slices 559-561 of FIG. 5B. The lead slices 570 and marker slices 571 (which collectively include imaging slices 555-561) each include an array of pixels. Each of the imaging slices 555-561 is arranged as an array of pixels with pixel locations within the array being identical (although offset from one another along the lead axis) for all of the imaging slices 555-561.

For each imaging slice, each pixel has an intensity corresponding to the amount of absorption of x-rays at a particular location along that imaging slice. For each imaging slice, the pixels with visible intensities approximately correspond to the lead-containing portions of that imaging slice, while the pixels that are dark tend to approximately correspond to regions of that imaging slice located outside of the lead. Additionally, pixels roughly corresponding to electrodes or conductors within the lead may be brighter than pixels roughly corresponding to the lead body.

Figure 6:
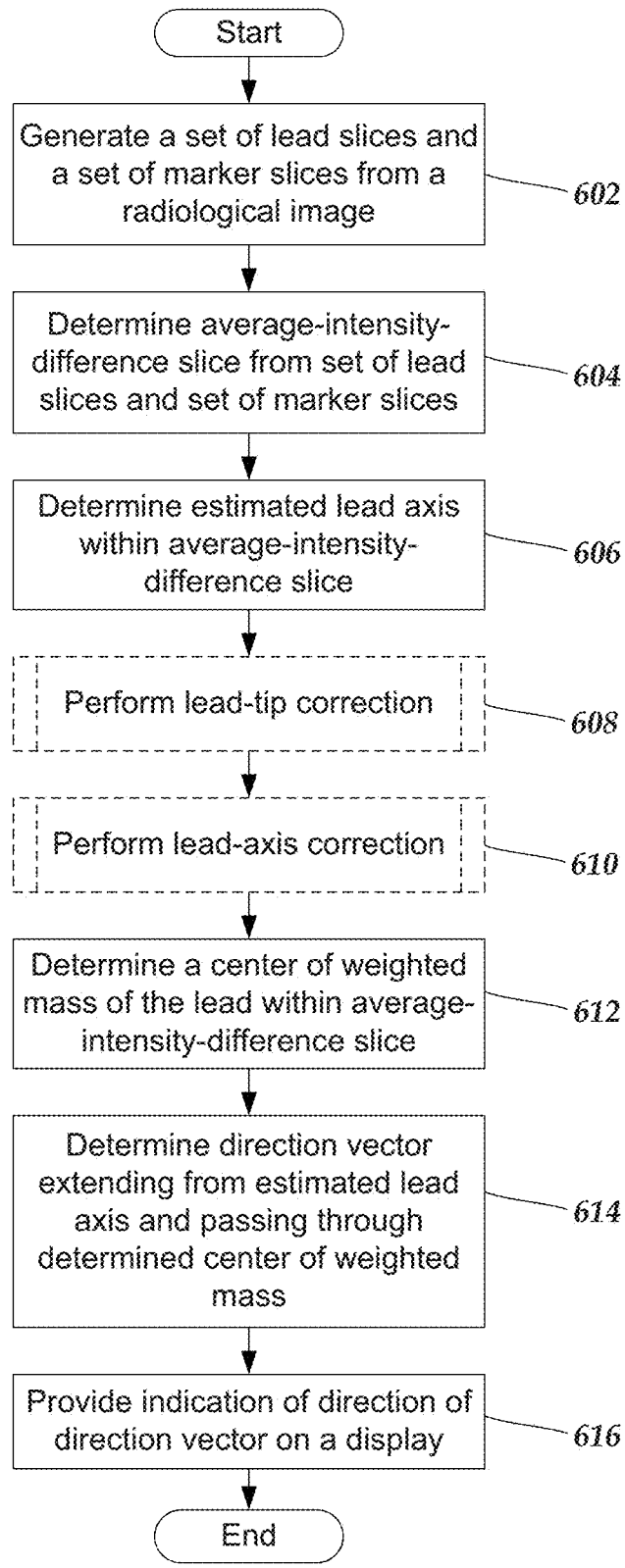
FIG. 6 is a flow chart of one embodiment of a method of determining a rotational orientation of a distal portion of a lead, according to the invention.

FIG. 6 illustrates one embodiment of a lead orientation determination algorithm. A direction vector is determined using the set of lead slices and the set of marker slices. The direction vector extends from an estimated lead axis and passes through a determined center of weighted mass of the lead. Steps 602-614 describe one embodiment of a technique for determining the location and direction of the direction vector.

In step 602, a set of lead slices and a set of marker slices are generated from a radiological image that includes a distal portion of a lead (e.g., 500 in FIGS. 5A-5B) that includes a distal tip (e.g., 542 in FIGS. 5A-5B), electrodes (e.g., 525 in FIGS. 5A-5B), and an asymmetric marker (e.g., 540 in FIGS. 5A-5B). The set of lead slices extend through the distal portion of the lead and include the portion of the lead along which the electrodes are disposed, and the set of marker slices extend through the portion of the lead along which the asymmetric marker is disposed. The lead slices and marker slices extend through the lead approximately transverse to the lead axis.

Lead tip and lead axis estimates can be obtained from the radiological image. In at least some embodiments, at least one of these estimates is obtained from scans of the lead in known orientations of the asymmetric marker and positioned at different angles to the CT scan planes. At least one of the lead tip or lead axis estimates can be obtained using a lead orientation determination algorithm, such as the lead orientation determination algorithm described below, or another lead orientation determination algorithm, such as described in U.S. Provisional Patent Applications Ser. Nos. 62/209,001 and 62/212,775, or some combination thereof.

In step 604, an average-intensity-difference slice is determined. The average-intensity-difference slice is formed, for each pixel location, by subtracting the intensity of that pixel of an average-marker-intensity slice from the intensity of that same pixel of an average-lead-intensity slice.

Figures 11, 12, 13:
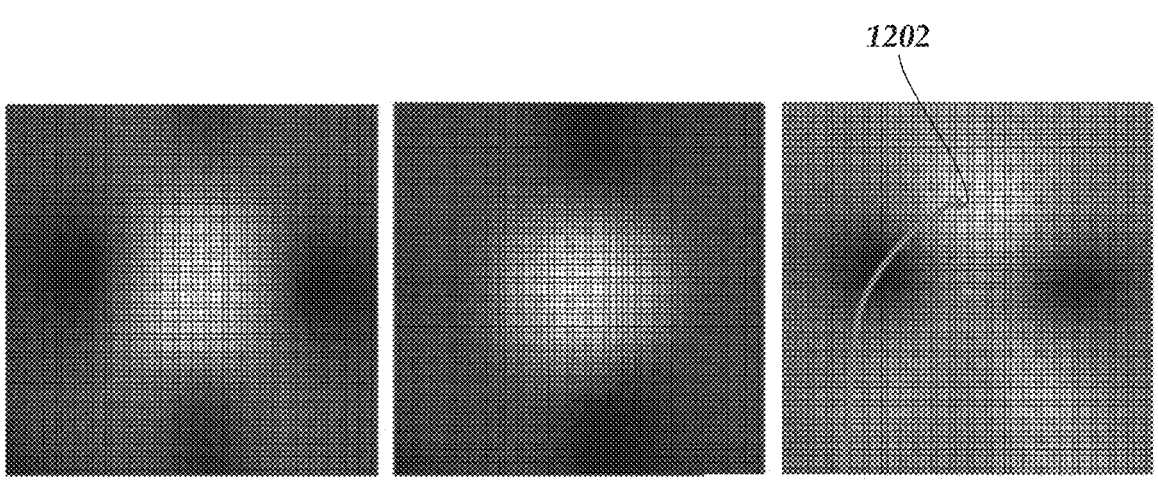
FIG. 11 is a schematic top view of one embodiment of an average-lead-intensity slice generated during performance of the method of FIG. 6, according to the invention.
FIG. 12 is a schematic top view of one embodiment of an average-marker-intensity slice generated during performance of the method of FIG. 6, according to the invention.
FIG. 13 is a schematic top view of one embodiment of an average-intensity-difference slice generated during performance of the method of FIG. 6, according to the invention.

The average-lead-intensity slice includes a calculated average intensity among each of the lead slices for each pixel location. FIG. 11 shows one embodiment of an average-lead-intensity slice. The average-marker-intensity slice includes a calculated average intensity among each of the marker slices for each pixel location. FIG. 12 shows one embodiment of an average-marker-intensity slice.

Optionally, every negative intensity value in the average-lead-intensity slice and average-marker-intensity slice can be set to zero to provide additional artifact suppression. FIG. 13 shows one embodiment of an average-intensity-difference slice.

In step 606, an estimated lead axis is determined within the average-intensity-difference slice. Optionally, in step 608, lead-tip-correction is performed to correct a lead tip estimate which, in turn, can refine the lead-axis estimate. A lead-tip-correction technique is described in more detail below, with reference to FIG. 7. Optionally, in step 610, lead-axis-correction is performed to correct the lead axis estimate. A lead-axis-correction technique is described in more detail below, with reference to FIG. 8.

In step 612, a calculated "center" (e.g., center of weighted mass, center-of-mass, calculated center-of-mass, or the like) is determined for the average-intensity-difference slice. The determination of the calculated "center" may include generating a center of weighted mass of the average-intensity-difference slice (e.g., weighting pixel intensities within a region of interest of the average-intensity-difference slice). For example, generating a center of weighted mass may involve squaring, or cubing pixel intensities (or taking other powers of pixel intensities) within a region of interest of the average-intensity-difference slice, and then finding the center-of-mass of the resulting slice. In other embodiments, weighting pixel intensities may involve using other functions (e.g., exponents, logarithms, roots, or the like) that are non-decreasing over positive numbers. In at least some embodiments the weighting is 1.

The region of interest is indicated by a bright spot corresponding to the asymmetric marker. A center-determining technique is described in more detail below, with reference to FIG. 10. FIGS. 15-18 show one embodiment of an exemplary average-intensity-difference slice undergoing a step-by-step performance of a center-determining technique.

In step 614, a direction vector is determined. The direction vector extends perpendicularly from the estimated lead axis and passes through the calculated "center" of the average-intensity-difference slice. In step 616, an indication of direction of the direction vector is provided on a display.

Figure 7:
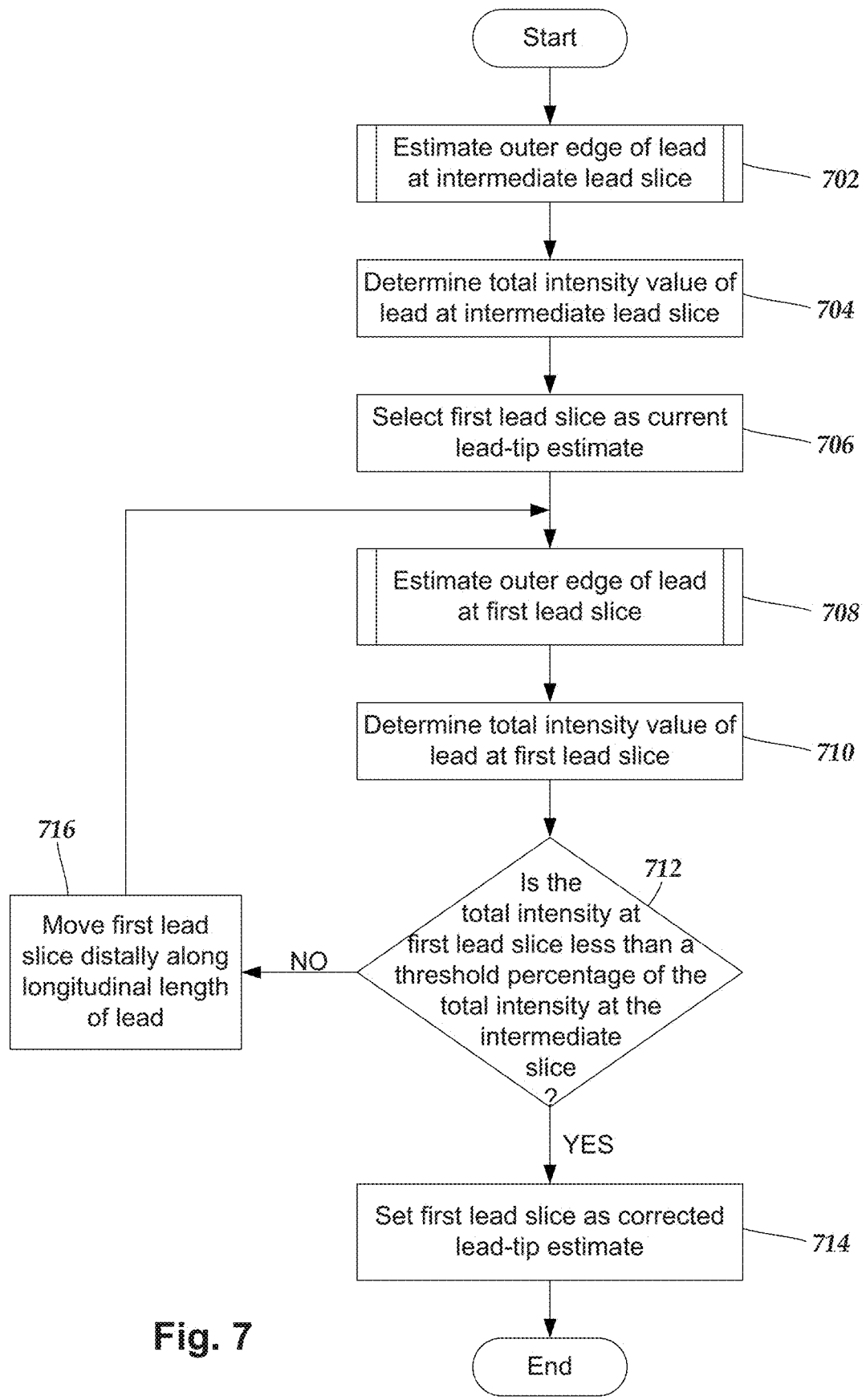
FIG. 7 is a flow chart of one embodiment of an optional lead-tip-correction step of the method of FIG. 6, according to the invention.

FIG. 7 illustrates one embodiment of a lead-tip-correction technique (step 608 of FIG. 6). The lead-tip-correction technique can be used to correct the lead-tip estimate. The lead-tip-correction technique may be performed multiple times until a corrected lead-tip estimate is obtained. The corrected lead-tip estimate can be used to refine the lead-axis estimate.

In step 702, for an intermediately-positioned slice of the set of lead slices (570 in FIG. 5A), an edge-detection technique is performed to estimate an outer edge of the lead in that slice. One embodiment of the edge-detection technique is described below, with reference to FIG. 9.

In at least some embodiments, the intermediate slice is positioned at the current estimate for the longitudinal midpoint of the electrode-containing portion of the lead (i.e., the imaging slice located halfway between the distal tip of the lead and the proximal edge of the proximal-most electrode). In at least one known suitable lead, this distance is 3.75 mm from the distal tip of the lead.

In step 704, a total intensity value is computed for the intermediate slice. The total intensity value is the total intensity of all the pixels located within the estimated lead outer edge, as determined, for example, by the edge-detection technique described below, with reference to FIG. 9.

In step 706, a first lead slice is selected from the set of lead slices as a current lead-tip estimate. The first lead slice is positioned distally along the lead from the intermediate slice. In step 708, an edge-detection technique is performed to estimate the outer edge of the lead in the first lead slice. One embodiments of a suitable edge-detection technique is described below, with reference to FIG. 9.

In step 710, a total intensity value is determined for the current lead-tip estimate. The total intensity value is the total intensity of all the pixels located within the estimated lead outer edge.

In step 712, when the total intensity value obtained in step 710 (the lead-tip estimate) is less than a threshold percentage of the total intensity value obtained in step 704 (an intermediate slice), then control is passed to step 714 and lead-tip estimate is updated as the corrected lead-tip estimate. The threshold percentage can be any percentage of the total intensity including, for example, 90%, 80%, 70%, 60%, 50%, 40%, 30%, 20%, 10% of the total intensity value obtained in step 704. In particular, a determined center of the lead-tip estimate is updated as the corrected lead-tip estimate. The center of the lead-tip estimate is determined based on all the pixels determined to be located within an estimated outer edge of the lead. Otherwise control is passed to step 716.

In step 716, the current lead-tip estimate is updated by selecting a new first lead slice positioned distally along a longitudinal length of the lead from the previous lead-tip estimate. In at least some embodiments, the new first lead slice is positioned two consecutive lead slices from the previous lead-tip estimate. In at least some embodiments, the distance between two consecutive slices is approximately 0.75 mm. The new first lead slice can be moved distally by other suitable increment including, for example, by an increment based on distance (e.g., 0.5 mm, 1 mm, 1.5 mm, 2 mm, or other distances), a slice-by-slice increment, every third consecutive slice, or other suitable increments.

Figure 8:
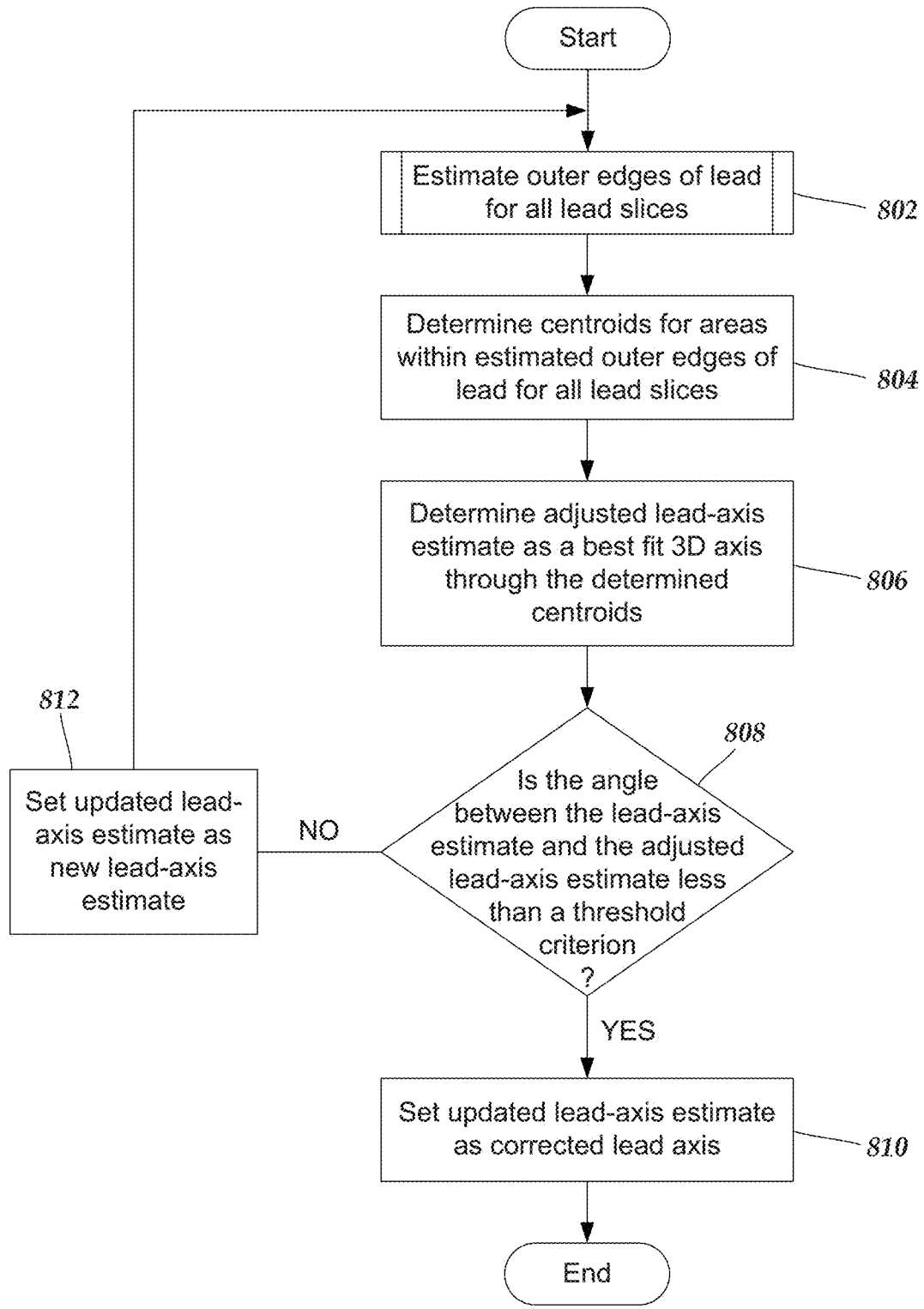
FIG. 8 is a flow chart of one embodiment of an optional lead-axis-correction step of the method of FIG. 6, according to the invention.

FIG. 8 illustrates one embodiment of a lead-axis-correction technique (step 610 of FIG. 6). The lead-axis-correction technique can be used to correct the lead-axis estimate (step 606 of FIG. 6). The lead-axis-correction technique can be performed multiple times until a corrected lead-axis estimate is obtained.

In step 802, for each of the set of lead slices (570 in FIG. 5A) an edge-detection technique is performed to estimate the outer edge of the lead at that slice. One suitable edge-detection technique is described below, with reference to FIG. 9. In step 804, for each slice of the set of lead slices (570 in FIG. 5A) a centroid is calculated based on all the pixels determined to be located within the estimated outer edge of the lead.

In step 806, a best-fit three-dimensional axis is calculated for the centroids determined in step 804. The best-fit three-dimensional axis is the adjusted lead-axis estimate. Any suitable technique can be used for calculating the best-fit three-dimensional axis. In at least some embodiments, a three-dimensional orthogonal distance regression is used for calculating the best-fit three-dimensional axis.

In step 808, if a threshold criterion is met, then control is passed to step 810, and the adjusted lead-axis estimate becomes the corrected lead axis. Otherwise, if the threshold criterion is not met, control is passed to step 812 and the adjusted lead-axis estimate becomes the current lead-axis estimate (step 606 of FIG. 6). In at least some embodiments, the threshold criterion is that the angle between a current lead-axis estimate (step 606 of FIG. 6) and the adjusted lead-axis estimate (of step 806) is less than 0.5 degrees. In other embodiments, the threshold criterion requires that the angle between the two estimates be less than some other amount including, for example, 0.1, 0.2, 0.3, 0.4, 0.6, 0.7, 0.8, 0.9, 1, 1.1, 1.2, 1.3, 1.4, 1.5 degrees, or more.

Figure 9:
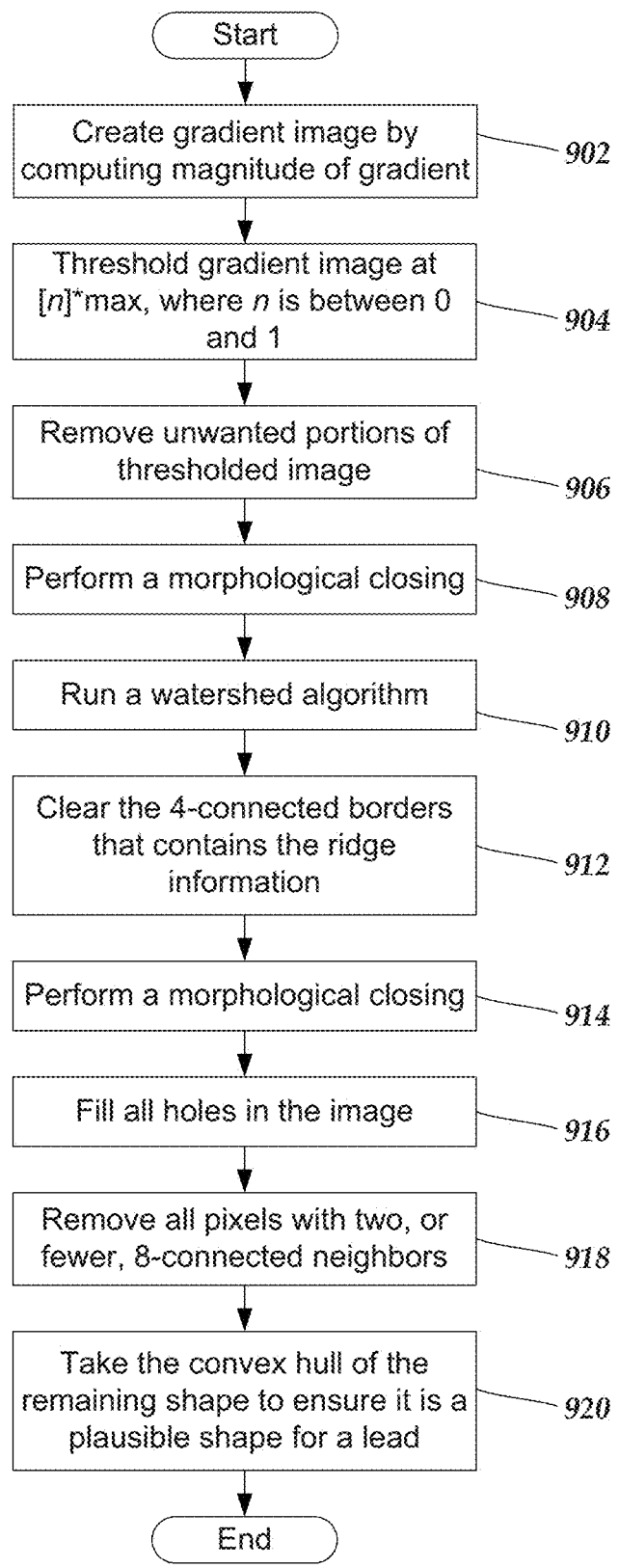
FIG. 9 is a flow chart of one embodiment of an edge-detection technique, according to the invention.

FIG. 9 illustrates one embodiment of an edge-detection technique utilized for estimating outer edges of the lead within a given imaging slice. For example, in previously-described steps 702, 708, and 802 an edge-detection technique is used to determine the outer edge of the lead. FIGS. 14A-14I show one embodiment of an exemplary lead slice undergoing a step-by-step performance of the below-described edge-detection technique.

In step 902, for each imaging slice of interest, a gradient image is formed by computing the magnitude of the gradient. The edge of interest (e.g., the outer edge of the lead) within the imaging slice(s) will occur where the gradient is steepest (see e.g., FIG. 14B).

Figure 14A:
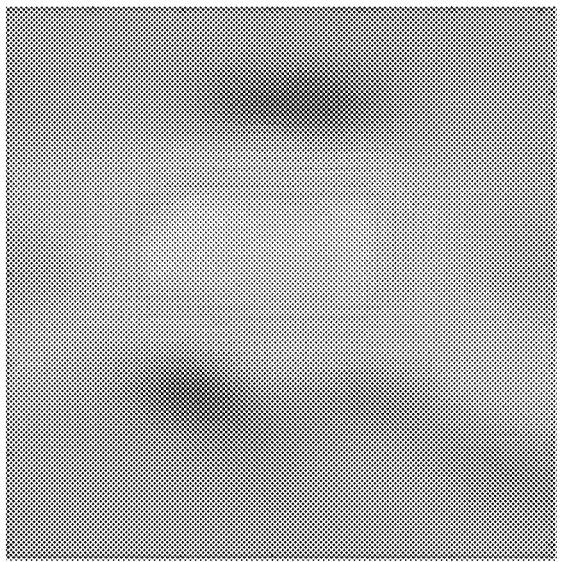
FIGS. 14A-14I are schematic top views of one embodiment of an imaging slice undergoing a step-by-step performance of the edge-detection technique of FIG. 9, according to the invention.
Figure 14B:
Figure 14C:
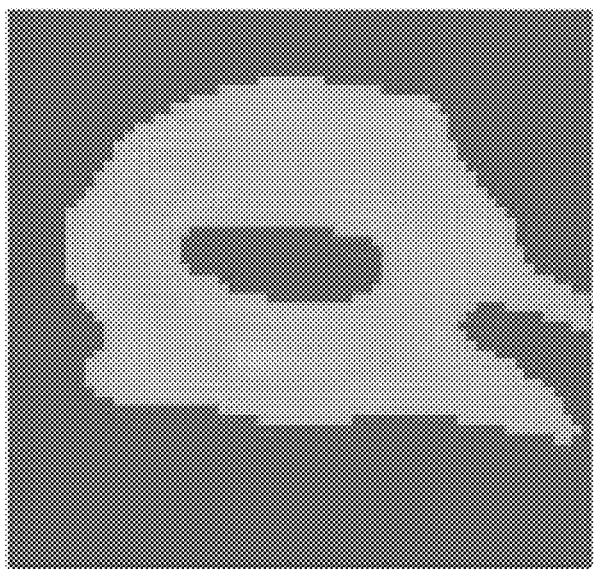

In step 904, for each imaging slice of interest, the gradient image is thresholded at [n]*max to remove some of the initial low-level noise and spurious edges, where n is between 0 and 1 (see e.g., FIG. 14C). In at least some embodiments, n is empirically chosen.

In step 906, for each imaging slice of interest, unwanted portions of the thresholded image are removed by further thresholding. In the case where the outer edge of the lead is being determined, the desired portion is the largest connected component in the thresholded image, which typically appears as an approximately elliptically-shaped region with a thick border. In which case, the unwanted portions are the portions that are not part of that elliptically-shaped region (see e.g., FIG. 14C).

Figure 14D:
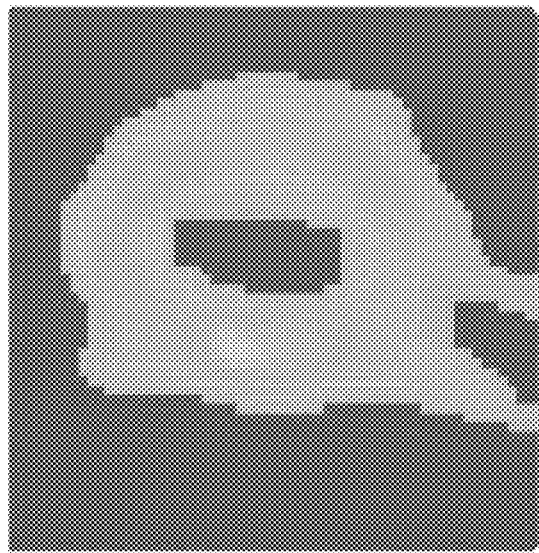

In step 908, for each imaging slice of interest, a morphological closing is performed using a 5×5 square structuring element to fix any undesired gaps in the largest connected component in the image (the approximately elliptically-shaped region with a thick border) (see e.g., FIG. 14D).

In step 910, for each imaging slice of interest, the watershed algorithm is run, considering only 4-connected neighbors to find the ridges of all the watershed areas in the image. In the case where the outer edge of the lead is being determined, the resulting image should be an approximately elliptically-shaped region with a one-pixel-thick border. In some instances, there may also be lines emanating from the approximately elliptically-shaped region or through the center-of-mass of the approximately elliptically-shaped region. Such lines are false edges and may be indicative of an undesired artifact (e.g., a streak) (see e.g., FIG. 14E).

In step 912, for each imaging slice of interest, the 4-connected borders of the binary image that contains the ridge information produced by the watershed algorithm are cleared. This will partly suppress the lines corresponding to false edges due to undesired artifacts, and will open the space in between two false edges so that it is no longer an area that is completely surrounded by pixels or the image border, (i.e., a hole) (see e.g., FIG. 14F).

Figure 14E:
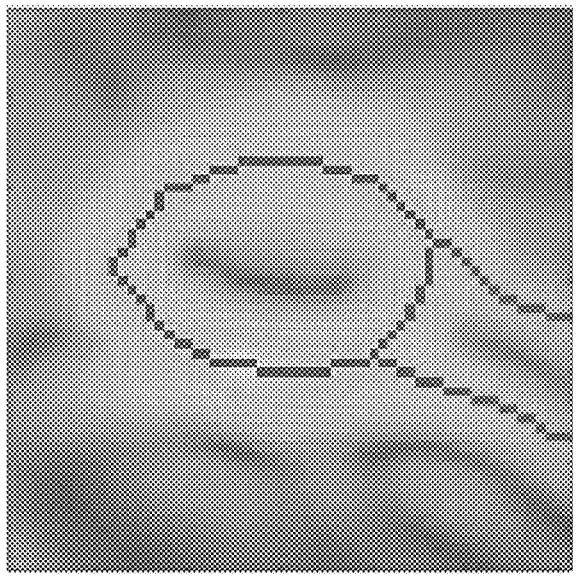
Figure 14F:
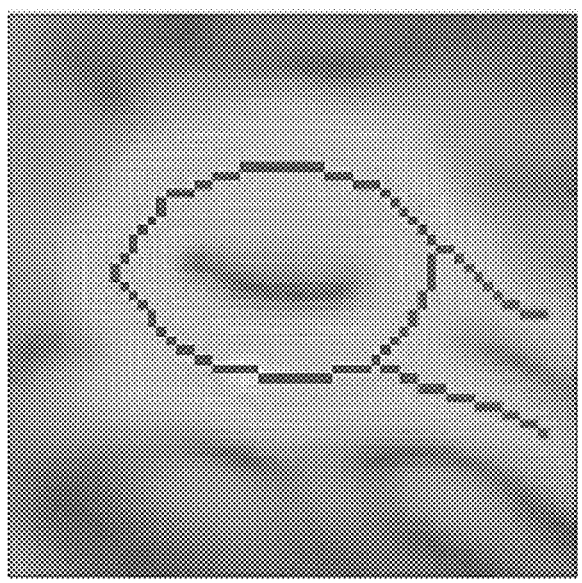
Figure 14G:
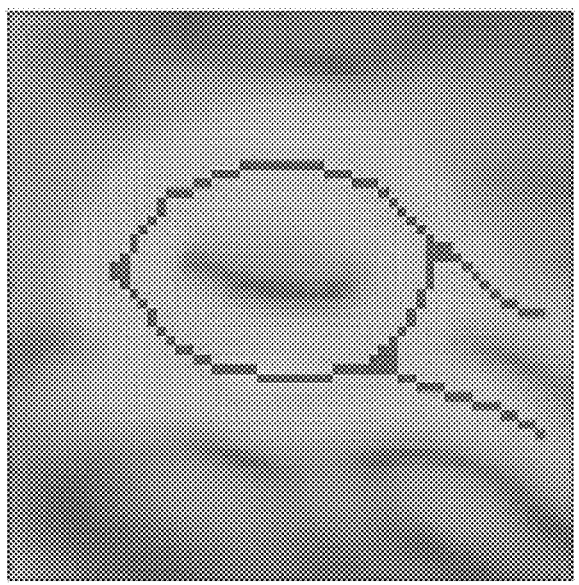

In step 914, for each imaging slice of interest, a morphological closing is performed using a 3×3 square structuring element to fix any undesired gaps created by clearing the 4-connected borders (see e.g., FIG. 14G).

In step 916, for each imaging slice of interest, all areas that are completely surrounded by pixels or the image border (i.e., holes) are filled. In the case where the outer edge of the lead is being determined, this will result in a filled approximately-elliptical shape (see e.g., FIG. 14H).

In step 918, for each imaging slice of interest, all pixels with two (or fewer) 8-connected neighbors are removed. This will completely suppress any remaining lines emanating from the region of interest (e.g., the approximately-elliptical shape), which constitute false edges due to undesired artifacts (see e.g., FIG. 14I).

In step 920, for each imaging slice of interest, the convex hull of the remaining shape is taken to ensure that the shape is plausible. In the case where the outer edge of the lead is being determined, any perpendicular slice through the lead should result in a convex shape. For the imaging slice of interest, the pixels around the border of the resulting convex shape correspond to the outer edge of the lead in that imaging slice.

Figure 10:
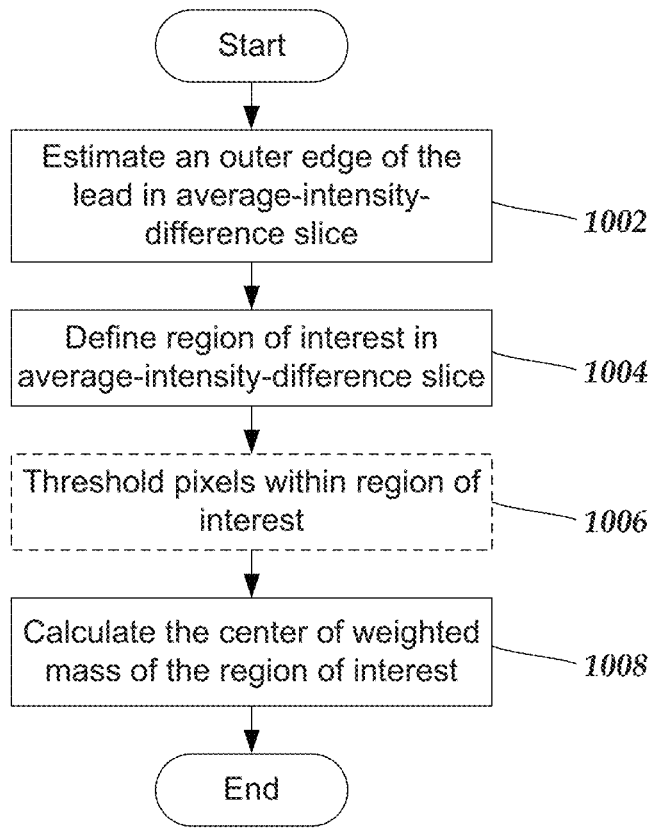
FIG. 10 is a flow chart of one embodiment of a center-determining technique for determining a center of weighted mass of the lead during performance of the method of FIG. 6, according to the invention.

FIG. 10 illustrates one embodiment of the center-determining technique (step 612 of FIG. 6). The center-determining technique is used for determining the calculated "center" (e.g., center of weighted mass, center-of-mass, calculated center-of-mass, or the like) of the average-intensity-difference slice. The calculated "center" of the average-intensity-difference slice is located within a region of interest, indicated by a bright spot, which corresponds to the asymmetric marker.

In step 1002, for the average-intensity-difference slice generated in step 604, an outer edge of the lead is estimated. This can be performed, for example, by performing the edge-detection technique (FIG. 9) to estimate the outer edge of an "average slice", such as the intermediate slice used in step 702, or by performing the edge-detection technique (FIG. 9) on all of the lead slices to obtain an estimated outer edge of an average lead slice determined in (see e.g., step 802).

In step 1004, the estimated outer edge is thickened by [n]*[lead radius], where n is between 0 and 1. This creates an approximately-elliptical shape that defines a region of interest corresponding to where the asymmetrical marker is located. The pixels located outside of this region of interest can be ignored (see e.g., FIG. 16).

Optionally, in step 1006, the remaining pixels are thresholded at [n]*[brightest pixel], where n is between 0 and 1. This removes dark areas from the region of interest that do not correspond to the asymmetrical marker (see e.g., FIG. 17).

In step 1008, the calculated "center" of the region of interest is determined. In at least some embodiments, the calculated "center" is a center-of-mass which, optionally, can be weighted ("center of weighted mass"). The weighing of the center of weighted mass is determined by applying a mathematical function to each pixel intensity value to put more emphasis on the brighter pixels and less emphasis on the less bright pixels. For example, each pixel intensity value can be raised to the nth power, where n is 1 or greater, and computing the center-of-mass of the resulting image. Other mathematical functions are possible for weighting the pixel intensity values in lieu of, or in addition to raising each pixel intensity value to the nth power (e.g., 2^[value], log[value], sqrt[value], or the like).

FIG. 11 illustrates one embodiment of an average-lead-intensity slice. The average-lead-intensity slice includes a calculated average intensity among each of the lead slices for each pixel location. FIG. 12 illustrates one embodiment of an average-marker-intensity slice. The average-marker-intensity slice includes a calculated average intensity among each of the marker slices for each pixel location.

FIG. 13 illustrates one embodiment of the average-intensity-difference slice generated in step 604. The average-intensity-difference slice is formed, for each pixel location, by subtracting the intensity of that pixel of an average-marker-intensity slice from the intensity of that same pixel of an average-lead-intensity slice.

The differences created by the asymmetry of the asymmetric marker to the rotationally symmetric electrodes form an off-center bright region 1202 in the average-intensity-difference slice. The bright region 1202 of the average-intensity-difference slice is the region of interest (step 1004) containing the asymmetric marker.

FIGS. 14A-14I illustrate an exemplary imaging slice undergoing a step-by-step performance of an edge-detection technique, as described above with reference to FIG. 9. FIG. 14A shows the imaging slice prior to edge detection. FIG. 14B shows the imaging slice as a gradient image after computing the magnitude of the gradient (step 902).

FIG. 14C shows the imaging slice after the gradient image is thresholded at [n]*max, where n is between 0 and 1, to remove some of the initial low-level noise and spurious edges, and the unwanted portions of the thresholded image are removed by further thresholding (steps 904, 906). FIG. 14D shows the imaging slice after a morphological closing is performed using a 5×5 square structuring element to fix any undesired gaps in the largest connected component in the image (step 908).

Figure 14H:
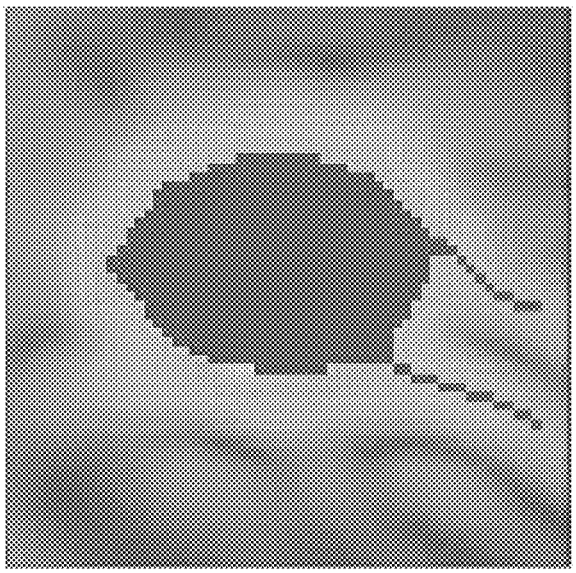
Figure 14I:
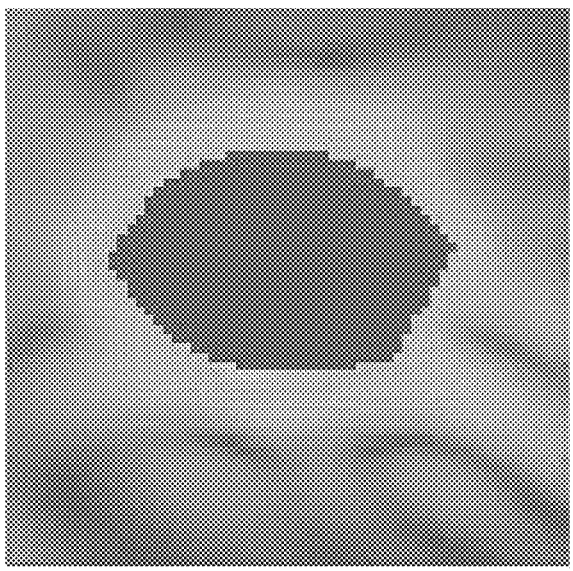

FIG. 14E shows the imaging slice after the watershed algorithm is run, considering only 4-connected neighbors to find the ridges of all the watershed areas in the image (step 910). FIG. 14F shows the imaging slice after the 4-connected borders of the binary image that contains the ridge information produced by the watershed algorithm are cleared (step 912). FIG. 14G shows the imaging slice after a morphological closing is performed using a 3×3 square structuring element to fix any undesired gaps created by clearing the 4-connected borders (step 914). FIG. 14H shows the imaging slice after all "holes" are filled (step 916). FIG. 14I shows the imaging slice after all pixels with two (or fewer) 8-connected neighbors are removed (step 918).

Figure 15:
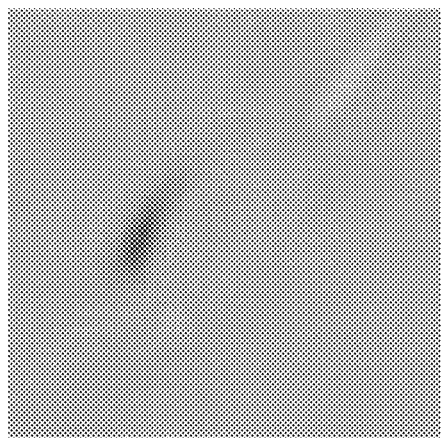
FIGS. 15-18 are schematic top views of one embodiment of an average-intensity-difference slice undergoing a step-by-step performance of the center-determining technique of FIG. 10, according to the invention.

FIGS. 15-18 show one embodiment of an exemplary average-intensity-difference slice undergoing a step-by-step performance of the center-determining technique. FIG. 15 illustrates one embodiment of an average-intensity-difference slice prior to performance of the center-determining technique.

Figure 16:
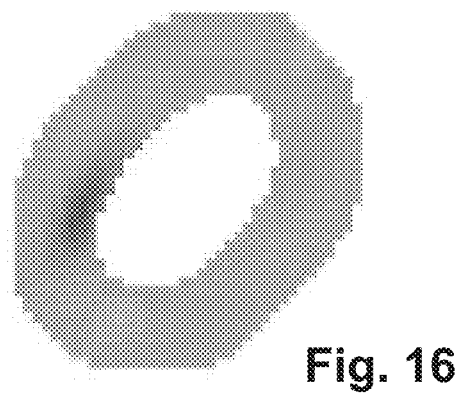
Figure 17:
Figure 18:

FIG. 16 illustrates one embodiment of the thickened outer edge with a region of interest that defines a region of interest corresponding to where the asymmetrical marker is located (step 1004). FIG. 17 illustrates one embodiment of the thresholded pixels within the region of interest (step 1006). FIG. 18 illustrates one embodiment of a direction vector extending perpendicularly from the lead-axis estimate and passing through the determined center of weighted mass of the average-intensity-difference slice.

Figure 19:
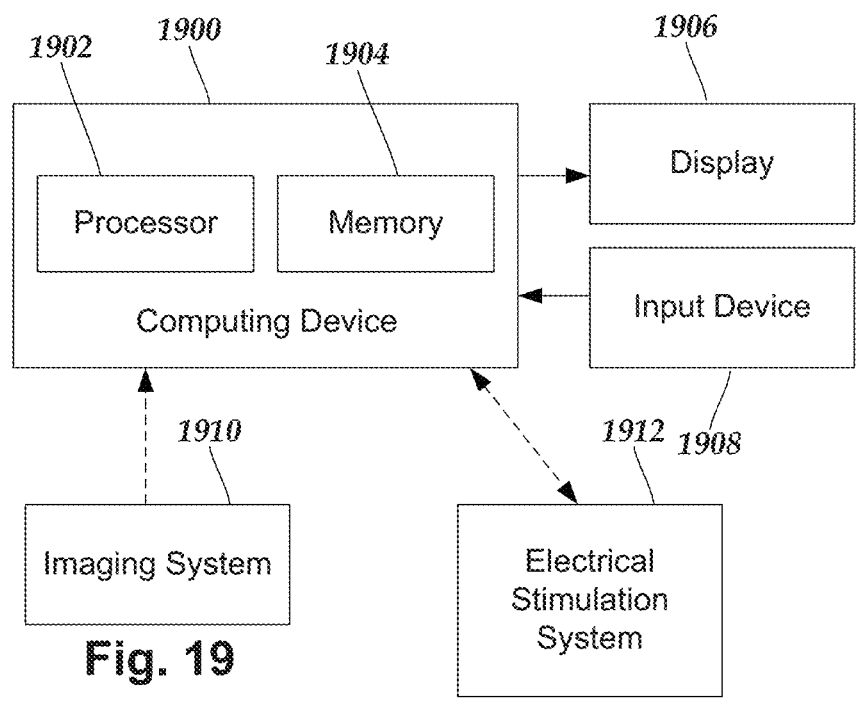
FIG. 19 is a schematic block diagram of one embodiment of a system for determining rotational orientation of a lead, according to the invention.

FIG. 19 illustrates one embodiment of a system for practicing the invention. The system can include a computing device 1900 or any other similar device that includes a processor 1902 and a memory 1904, a display 1906, an input device 1908, and, optionally, the electrical stimulation system 1912 (such as the system 10 in FIG. 1). The system 1900 may also optionally include one or more imaging systems 1910 (for example, a CT imaging system). In some embodiments, the computing device 1900 is part of the imaging system 1910. In some embodiments, the computing device 1900 is part of the electrical stimulation system 1912, such as part of the clinician programmer 18 (FIG. 1), remove control 16 (FIG. 1), or external trial stimulator 20 (FIG. 1). In other embodiments, the computing device 1900 is not part of either the electrical stimulation system 1912 or imaging system 1910.

The computing device 1900 can be a computer, tablet, mobile device, or any other suitable device for processing information. The computing device 1900 can be local to the user or can include components that are non-local to the computer including one or both of the processor 1902 or memory 1904 (or portions thereof). For example, in some embodiments, the user may operate a terminal that is connected to a non-local computing device. In other embodiments, the memory can be non-local to the user.

The computing device 1900 can utilize any suitable processor 1902 including one or more hardware processors that may be local to the user or non-local to the user or other components of the computing device. The processor 1902 is configured to execute instructions provided to the processor.

Any suitable memory 1904 can be used for the computing device 1902. The memory 1904 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 1906 can be any suitable display device, such as a monitor, screen, display, or the like, and can include a printer. The input device 1908 can be, for example, a keyboard, mouse, touch screen, track ball, joystick, voice recognition system, or any combination thereof, or the like.

One or more imaging systems 1910 can be used including, but not limited to, MRI, CT, ultrasound, or other imaging systems. The imaging system 1910 may communicate through a wired or wireless connection with the computing device 1900 or, alternatively or additionally, a user can provide images from the imaging system 1910 using a computer-readable medium or by some other mechanism.

The electrical stimulation system 1912 can include, for example, any of the components illustrated in FIG. 1. The electrical stimulation system 1912 may communicate with the computing device 1900 through a wired or wireless connection or, alternatively or additionally, a user can provide information between the electrical stimulation system 1912 and the computing device 1900 using a computer-readable medium or by some other mechanism. In some embodiments, the computing device 1900 may include part of the electrical stimulation system, such as, for example, the IPG, CP, RC, ETS, or any combination thereof.

One or more images or imaging data, for example, CT images or imaging data, can be provided to, or generated by, the computing device 1900. The images or imaging data can be provided by the imaging system 1910 or any other suitable image source.

With respect to lead determination methods that utilize isosurfaces, the computing device can produce an isosurface image, as illustrated in FIGS. 5A-5B. Alternatively, the isosurface image can be provided to the computing device 1900 from the imaging system 1910 or any other suitable source. In at least some embodiments, the computing device 1900 displays the isosurface image on the display 1906. The isosurface image may be based on a user-specified isovalue (or narrow range around the user-specified isovalue) or may be based on a default or predefined isovalue (or narrow range around the isovalue). In some embodiments, the computing device 1900 provides a user interface for receiving the user-specified isovalue as an input. In some embodiments, the user interface can include a slider bar, or other mechanism, that allows the user to change the isovalue and see the resulting isosurface image. In at least some embodiments, at low isovalues voxels corresponding to the skull and the brain may be included in the isosurface image. In at least some embodiments, to avoid this, the system may require that the user-specified isovalue meet or exceed a threshold (for example, a threshold of 1900 or 30% of the peak Hounsfield unit or any other suitable value).

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each of the methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a set of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A method for identifying a rotational orientation of an implanted electrical stimulation lead, the method comprising:
    generating, from a radiological image of a distal portion of a lead, a set of lead slices and a set of marker slices, the lead comprising a lead body, a distal tip, a plurality of electrodes disposed along a distal portion of the lead body, and an asymmetric marker disposed along the distal portion of the lead body, the plurality of electrodes comprising a plurality of segmented electrodes that each extend around no more than 50% of a circumference of the lead body, wherein the lead defines a lead axis extending along a portion of the lead that extends from the distal tip and includes the plurality of electrodes and the asymmetric marker;
    determining, using the set of lead slices and the set of marker slices, a direction vector extending from an estimated lead axis and passing through a determined center of weighted mass of the lead; and
    providing an indication of a direction of the direction vector on a display.

2. The method of claim 1, wherein generating, using the radiological image, a set of lead slices and a set of marker slices comprises generating the set of lead slices each extending through the distal portion of the lead transverse to the lead axis at a longitudinal position along the lead ranging from the distal tip to a proximal edge of a proximal-most one of the electrodes.

3. The method of claim 1, wherein generating, using the radiological image, a set of lead slices and a set of marker slices comprises generating the set of marker slices each extending through the distal portion of the lead transverse to the lead axis at a longitudinal position along the lead where a marker window is disposed.

4. The method of claim 1, wherein determining, using the set of lead slices and the set of marker slices, a direction vector extending from an estimated lead axis and passing through a determined center of weighted mass of the lead comprises:
    determining, using the set of lead slices and the set of marker slices, an average-intensity-difference slice;
    determining the estimated lead axis of the lead within the average-intensity-difference slice; and
    determining the center of weighted mass of the lead within the average-intensity-difference slice.

5. The method of claim 4, wherein each of the plurality of lead slices and marker slices is arranged as an array of pixels with pixel locations within the array being identical for all of the lead slices and marker slices, with each particular pixel location being offset from the corresponding pixel location of other lead slices and marker slices along the lead axis.

6. The method of claim 5, wherein determining an estimated lead axis of the lead within the average-intensity-difference slice comprises obtaining a lead-tip estimate.

7. The method of claim 6, wherein obtaining a lead-tip estimate comprises performing lead-tip-correction to generate a corrected lead-tip estimate; the lead-tip-correction comprising
    (a) estimating, for an intermediately-positioned lead slice of the set of lead slices, an outer edge of the lead;
    (b) determining, for the intermediately-positioned lead slice, a total intensity value of all the pixels located within the estimated outer edge of the lead;
    (c) selecting a first lead slice, of the set of lead slices, distal to the intermediately-positioned lead slice as a current lead-tip estimate;
    (d) estimating, for the first lead slice, an outer edge of the lead;
    (e) determining, for the first lead slice, a total intensity value of all the pixels located within the estimated outer edge of the lead; and
    (f) setting the first lead slice as a corrected lead-tip estimate when the total intensity value for the first lead slice is less than a threshold percentage of the total intensity value for the intermediately-positioned lead slice, or updating a location of the current lead-tip estimate to a different lead slice, of the set of lead slices, that is positioned more distally along the lead from the first lead slice when the total intensity value for the first lead slice is equal to or greater than the threshold percentage of the total intensity value for the intermediately-positioned lead slice.

8. The method of claim 7, wherein (a) estimating, for an intermediately-positioned lead slice, an outer edge of the lead comprises selecting an intermediately-positioned lead slice located at a midpoint along the lead between the distal tip and a proximal edge of a proximal-most electrode.

9. The method of claim 7, wherein estimating an outer edge of the lead for each of steps (a) and (c) comprises performing an edge-detection technique.

10. The method of claim 7, wherein (c) setting the first lead slice as the corrected lead-tip estimate comprises setting a determined centroid of the first lead slice as the corrected lead-tip estimate.

11. The method of claim 5, wherein determining an estimated lead axis of the lead within the average-intensity-difference slice comprises performing lead-axis correction to generate a corrected lead-axis estimate, the lead-axis-correction comprising:
    (a) obtaining a current lead-axis estimate;
    (b) estimating, for each lead slice of the set of lead slices, an outer edge of the lead for that slice;
    (c) determining, for each lead slice of the set of lead slices, a centroid for the pixels within the estimated outer edge of the lead;
    (d) determining a best-fit three-dimensional axis for the determined centroids to provide an updated lead-axis estimate; and
    (e) setting the updated lead-axis estimate as the corrected lead axis when an angle between the current lead-axis estimate and the updated lead-axis estimate meets a threshold criterion, or when the threshold criterion is not met, replacing the current lead-axis estimate with the updated lead-axis estimate.

12. The method of claim 11, wherein setting the updated lead-axis estimate as the corrected lead axis when an angle between the current lead-axis estimate and the updated lead-axis estimate meets a threshold criterion comprises setting the updated lead-axis estimate as the corrected lead axis when an angle between the current lead-axis estimate and the updated lead-axis estimate is less than 0.5 degrees.

13. The method of claim 11, wherein determining a best-fit three-dimensional axis for the determined centroids to provide an updated lead-axis estimate comprises performing a three-dimensional orthogonal distance regression.

14. The method of claim 11, wherein replacing the current lead-axis estimate with the updated lead-axis estimate comprises repeating steps (b) through (e).

15. The method of claim 5, wherein determining, using the set of lead slices and the set of marker slices, an average-intensity-difference slice comprises:
    determining, for the set of lead slices, an average-lead-intensity at each pixel location to obtain an average-lead-intensity slice;
    determining, for the set of marker slices, an average-marker-intensity at each pixel location to obtain an average-marker-intensity slice; and
    subtracting, for each pixel location, the average-lead-intensity from the average-marker-intensity to determine the average-intensity-difference slice.

16. The method of claim 15, further comprising setting to zero every pixel of each of the average-lead-intensity slice and the average-marker-intensity slice having a negative intensity value.

17. The method of claim 5, wherein determining a center of weighted mass of the lead within the average-intensity-difference slice comprises:
    determining, for the average-intensity-difference slice, an estimated outer edge of the lead;
    determining an inner edge of the asymmetric marker to define a region of interest within which the asymmetric marker is located; and
    calculating a center of weighted mass of the region of interest.

18. The method of claim 17, further comprising thresholding the region of interest at a predetermined level to remove dark areas within the region of interest prior to calculating the center of weighted mass of the region of interest.

19. A system for identifying a rotational orientation of an implanted electrical stimulation lead, the system comprising:
    a computer processor configured and arranged to perform the method of claim 1.

20. A non-transitory computer-readable medium having computer executable instructions stored thereon that, when executed by a processor, cause the processor to perform the method of claim 1.

* * * * *